United States Patent
Smith

[11] Patent Number: 5,879,333
[45] Date of Patent: Mar. 9, 1999

[54] CATHETER WITH BODY LOCKING INTO CANNULA HUB

[75] Inventor: Ross Cyril Smith, Greenwich, Australia

[73] Assignee: Microcatheters Pty Ltd, Greenwich, Australia

[21] Appl. No.: 945,327
[22] PCT Filed: Apr. 23, 1996
[86] PCT No.: PCT/AU96/00236
§ 371 Date: Oct. 23, 1997
§ 102(e) Date: Oct. 23, 1997
[87] PCT Pub. No.: WO96/33764
PCT Pub. Date: Oct. 31, 1996

[30] Foreign Application Priority Data

Apr. 24, 1995 [AU] Australia .................... PN2558

[51] Int. Cl.$^6$ ........................................ A61M 5/00
[52] U.S. Cl. ........................ 604/164; 604/165; 604/51
[58] Field of Search ........................ 604/164, 165, 604/166, 280–283, 264, 49, 51, 52, 53

[56] References Cited

U.S. PATENT DOCUMENTS 4,931,039  6/1990  Coe et al. .

FOREIGN PATENT DOCUMENTS

| 56832/69 | 12/1970 | Australia . |
| 49988/79 | 2/1980 | Australia . |
| 51392/79 | 4/1980 | Australia . |
| 48686/93 | 4/1994 | Australia . |

*Primary Examiner*—John D. Yasko
*Attorney, Agent, or Firm*—Browdy and Neimark

[57] ABSTRACT

A system for introducing a fine bore catheter into a vein includes a cannula unit comprising an elongate tubular sheath, defining a distal end and a proximal end, and a hub enclosing the proximal end of the sheath. The cannula unit is adapted to receive an introducing needle for introducing the distal end of the sheath of the cannula into a vein. The system also includes a catheter unit, having a distal end and a proximal end, a body portion located at the proximal end of the catheter unit, and a catheter tube extending from the body portion to the distal end of the catheter unit. The hub of the cannula unit defines guide means adapted to receive and guide the distal end of the catheter tube into the proximal end of the cannula sheath so that the catheter tube can be guided into and then fed along the sheath, and the hub of the cannula is adapted to receive and enclose at least a portion of the body of the catheter in a locking arrangement which substantially prevents the catheter body moving relative to the hub of the cannula unit.

18 Claims, 4 Drawing Sheets

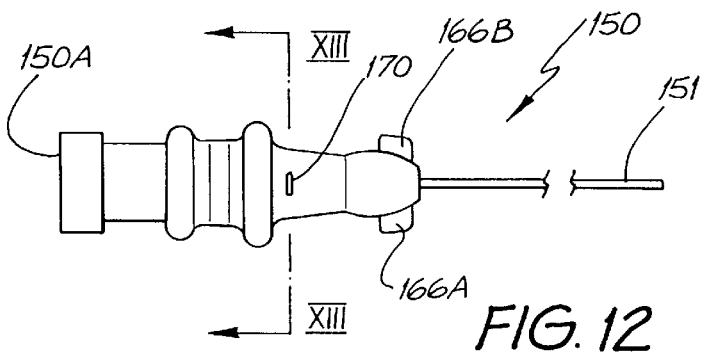
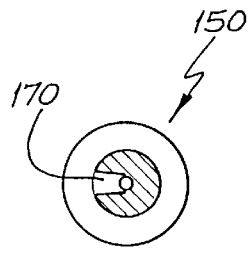
FIG. 12  FIG. 13
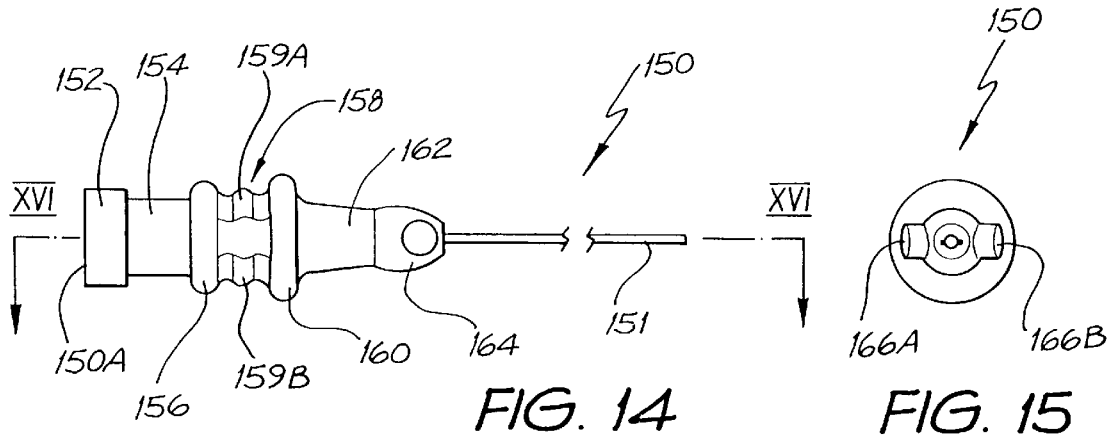
FIG. 14  FIG. 15
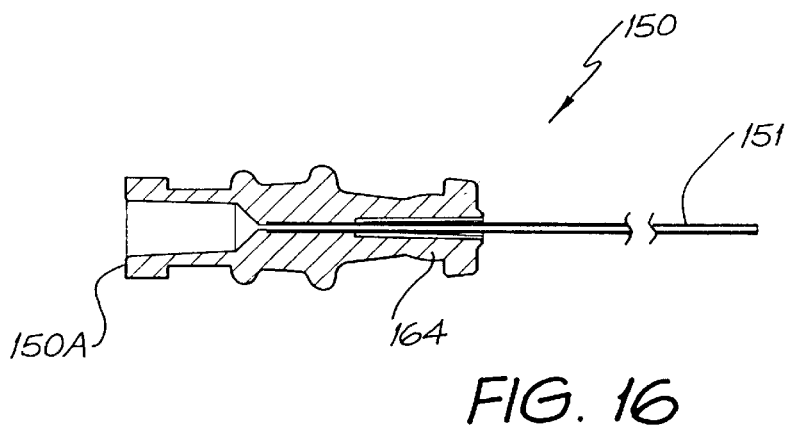
FIG. 16

CATHETER WITH BODY LOCKING INTO CANNULA HUB

This application is a 371 of PCT/AU96/00236 filed Apr. 23,1996.

FIELD OF THE INVENTION

This invention relates to fine bore catheter and to a system for inserting a fine bore catheter into a vein.

BACKGROUND OF THE INVENTION

As used in this specification and in the appended claims, the term fine bore catheter tube means a catheter tube having an outside diameter of less than 2.0 mm and an internal bore of less than 1.5 mm. Similarly fine bore catheter means a catheter having a fine bore catheter tube.

Fine-bore silicone catheters allow long term phlebitis (inflammation) free infusion of intravenous nutrition into peripheral veins such as leg and arm veins. They also create less trauma to a patent's body tissue than a larger bore catheter and have a wider range of applications than a larger bore catheter. Such a fine-bore catheter can be as effective as a larger bore catheter centrally placed in a main vein in the torso or chest of a patient such as infraclavicular sub clavian or jugular vein. Placing a larger catheter in a main vein has inherent risks: in particular sepsis and thrombosis can occur. Dedicated specialised support teams are required to monitor patients subjected to central venous cannulation yet the risks persist. However, because of the problems associated with introducing fine bore catheters into peripheral veins, central venous cannulation, despite the potentially life threatening risks, remains the current method of choice for administration of intravenous nutrition.

The current method of placing catheters in peripheral veins requires taxing hand to eye coordination and uses risky "catheter through needle" techniques with which it is possible to cut the catheter tube on the needle being used to introduce the catheter in a peripheral vein and thus requires specially trained personnel. Hence central venous cannulation despite the potential life threatening risks remains the current method of choice for administration of intravenous nutrition.

The present invention seeks to provide an improved system for the insertion of very fine catheters into veins, particularly peripheral veins

SUMMARY OF THE INVENTION

According to the present invention there is provided a system for introducing a fine bore catheter into a vein including:

a cannula unit comprising an elongate tubular sheath, the sheath defining a distal end and a proximal end, the cannula unit further comprising a hub enclosing the proximal end of the sheath, the cannula unit being adapted to receive an introducing needle for introducing the distal end of the sheath of the cannula into a vein; and a catheter unit, the catheter unit having a distal end and a proximal end, a body portion located at the proximal end of the catheter unit, and a catheter tube extending from the body portion to the distal end of the catheter unit characterised in that the catheter tube is a fine bore catheter tube, in that the hub of the cannula unit defines guide means adapted to receive and guide the distal end of the catheter tube into the proximal end of the cannula sheath so that the catheter tube can be guided into and then fed along the sheath, and in that the hub of the cannula is adapted to receive and enclose at least a portion of the body of the catheter in a locking arrangement which substantially prevents the catheter body moving relative to the hub of the cannula unit.

Conveniently the proximal end of the catheter defines a luer lock or similar means for attaching the proximal end of the catheter to a syringe or other fluid delivery device.

It is preferred that the bore of the lumen of the catheter is of constant diameter from the proximal end to the distal end. This reduces the risk of blood products clotting the bore of the lumen.

It is preferred that the external diameter of the catheter is between 0.6 mm and 1.2 mm.

The internal bore of the catheter may be 0.3 to 0.8 mm.

It is preferred that the system includes a introducing needle for insertion into the cannula for piercing a vein. The needle comprises a needle having a distal end adapted to pierce a vein and the proximal end of the needle is mounted in a hollow hub.

The invention also provides a catheter unit, having a distal end and a proximal end, including a body portion located at the proximal end of the catheter unit, and a catheter tube extending from the body portion to the distal end of the catheter unit characterised in that the catheter tube is a fine bore catheter tube, and in that at least a portion of the body of the catheter is adapted to be received and enclosed in the hub of a cannula in a locking arrangement which substantially prevents the catheter body moving relative to the hub of the cannula unit.

The invention also provides a cannula unit for use in conjunction with the catheter as described above comprising an elongate tubular sheath, the sheath defining a distal end and a proximal end, the cannula unit further comprising a hub enclosing the proximal end of the sheath, the cannula unit being adapted to receive an introducing needle for introducing the distal end of the sheath of the cannula into a vein; and characterised in that the hub of the cannula unit defines guide means adapted to receive and guide the distal end of a catheter tube into the proximal end of the cannula sheath so that the catheter tube can be guided into and then fed along the sheath, and in that the hub of the cannula is adapted to receive and enclose at least a portion of the body of the catheter in a locking arrangement which substantially prevents the catheter body moving relative to the hub of the cannula unit.

Although the present invention is particularly suited to use with fine bore catheters the structure of the system can also be used with large bore diameter catheters. Thus the present invention also provides a system for introducing a catheter into a vein including:

cannula unit comprising an elongate tubular sheath the sheath defining a distal end and a proximal end, the cannula unit further comprising a hub enclosing the proximal end of the sheath, the cannula unit being adapted to receive an introducing needle for introducing the distal end of the sheath of the cannula into a vein; and a catheter unit, the catheter unit having a distal end and a proximal end, a body portion located at the proximal end of the catheter unit, and a catheter tube extending from the body portion to the distal end of the catheter unit characterised in that the hub of the cannula unit defines guide means adapted to receive and guide the distal end of the catheter tube into the proximal end of the cannula sheath so that the catheter tube can be guided into and then fed along the sheath, and in that the hub of the cannula is adapted to receive and enclose at least a portion of the body of the catheter in a locking arrangement which substantially prevents the CF body moving relative to the hub of the cannula unit.

BRIEF DESCRIPTION OF THE DRAWINGS

The invention will now be described by way of example only and with reference to the accompanying drawings in which:

FIG. 12 is a plan view of the catheter shown in FIG. 5;

FIG. 13 is a sectional view on line XIII—XIII of FIG. 12:

FIG. 14 is a side elevation of the catheter shown in FIG. 12:

FIG. 15 is a front view of the catheter shown in FIG. 12: and

FIG. 16 is a sectional view on lines XVI—XVI shown in FIG. 15.

SPECIFIC DESCRIPTION OF THE BEST METHOD FOR PERFORMING THE INVENTION

Figure 1:
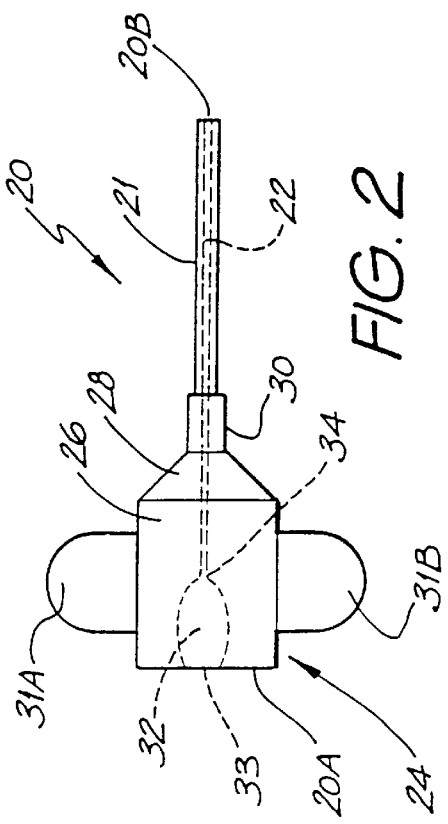
FIG. 1 is a schematic drawing of an introducing needle unit.

Referring to the drawings, the principle of operation of the present invention will be described with reference to FIGS. 1 to 4.

FIG. 1 shows an introducing needle unit, or trocar, 10. The needle unit includes a stainless steel needle 11 having a distal end 12 defining a bevel portion which is adapted to pierce a vein or the like. The other, or proximal end, 13 of the needle is embedded in a hub 14. The hub 14 is rotationally symmetrical about the longitudinal axis defined by the needle 11 and includes a clear flash back chamber 16. The proximal end 17 of the needle unit is open but is adapted to receive a breathing filter or stopper, if required. The distal end 18 of the hub is semi ellipsoid in shape.

Figure 2:
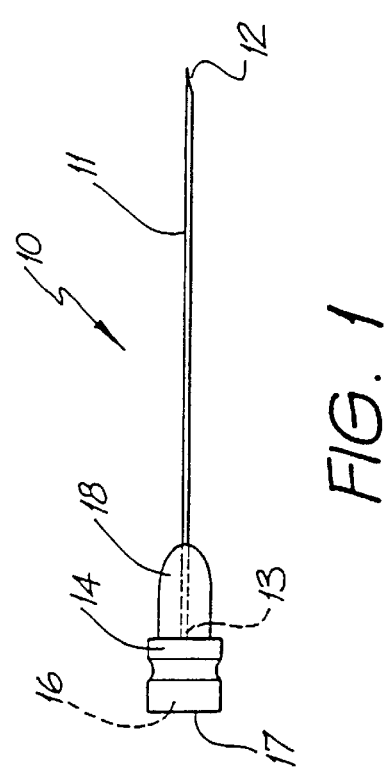
FIG. 2 is a schematic drawing of a cannula unit.

FIG. 2 shows an introducing cannula unit 20. The cannula unit includes an elongate sheath, or tube 21 having an annular cross section and defining a cylindrical bore 22. The cannula unit has a proximal end 20A and a distal end 20B. The tube 21 is embedded in a hub 24. The hub is generally rotationally symmetrical about a longitudinal axis defined by the elongate tube 21. From the proximal end 20A the hub defines a main body portion 26 which is cylindrical, a conical portion 28 which tapers towards to a further cylindrical portion 30 which is substantially narrower than the main body portion 26 and has a slightly larger diameter than the outside diameter of the elongate tube.

Two diametrically opposed planar wings 31A, 31B extend outwards from the main body portion 26 in a plane parallel to and passing through the longitudinal axis defined by the tube 21.

As is shown in phantom (i.e. in broken lines) at the proximal end 20A of the cannula unit, the hub defines a cavity 32 which is in the shape of a truncated ellipsoid. The proximal or open end 33 of the cavity is of a reduced diameter compared with the maximum diameter of the ellipsoid. The narrower end of the cavity 34, being the end distal from the proximal end of the cannula tapers gradually to define a bore which is the same diameter as the bore 22 of the tube. The tube 21 extends into the hub as far as that end 34 of the cavity.

The hub is made of a plastics material and thus is deformable The ellipsoid cavity is dimensioned so that the distal end 18 of the hub of the needle unit will securely locate in the cavity, with some deformation of the hub.

The length of the tube 21 is such that if the needle unit is inserted through the tube 21 with the distal portion 18 of the hub located in the cavity 32, the distal end or bevel portion 12 of the needle will just protrude from the distal end 20B of the tube 21.

Figure 3:
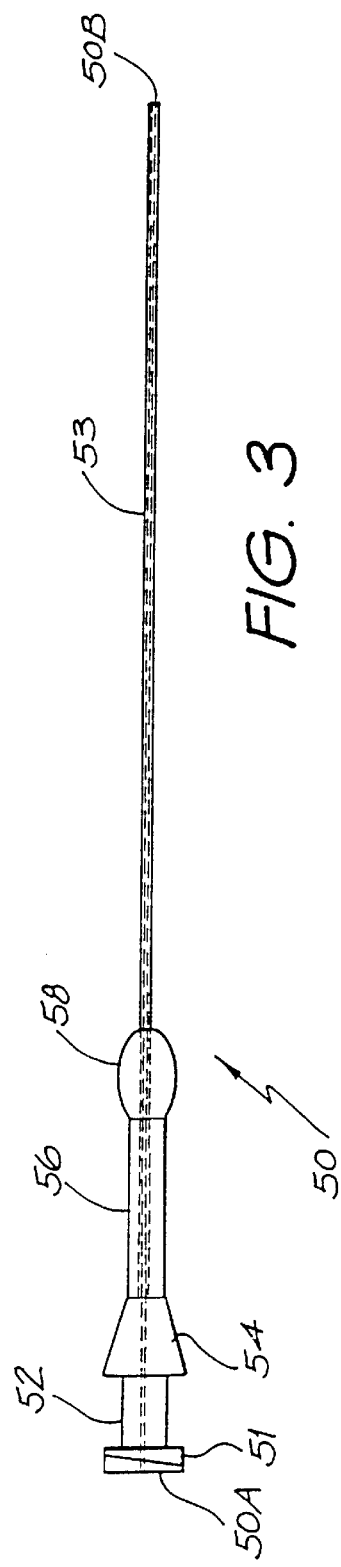
FIG. 3 is a schematic drawing of a catheter unit.
Figure 4:
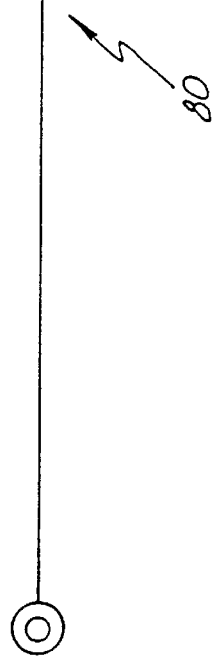
FIG. 4 is a guide wire.

FIG. 3 shows a fine bore catheter 50 and FIG. 4 shows a guide wire 80 for use with that catheter 50.

The catheter has a proximal end 50A and a distal end 50B.

At the proximal end 50A of the catheter, there is a luer lock 51 to enable the proximal end 50A of the catheter to be connected to a syringe, or the like. From the luer lock to the distal end of the catheter, the catheter body comprises a first cylindrical portion 52 which is stepped out to the base of a truncated conical section 54, which tapers to a further cylindrical portion 56 followed by a generally ellipsoid protrusion or plug 58. A fine bore silicone catheter tube 53 having an external diameter of 1.1 mm and an internal bore of diameter 0.8 mm extends from the junction of the conical portion 54 and the cylindrical portion 56 of the catheter body through the ellipsoid portion 58 and extends beyond that ellipsoid portion. The total length of the fine bore catheter tube is approximately 150 mm.

In use, the introducing needle unit 10 shown in FIG. 1 is fitted into the introducing cannula unit 20 with the ellipsoid portion 18 fitting into the cavity 32 to securely locate the needle unit in the cannula unit. The distal end 12 of the needle 11 protrudes just beyond the distal end 20B of the elongate tube 21 of the introducing cannula unit. The needle can then be used to insert the tube 21 of the cannula unit into a peripheral vein of a patient. The clear hub 16 allows the person inserting the cannula into the vein to see when blood flashes back into the hub 16 which indicates that the cannula is located in the vein. The needle unit is then removed from the cannula unit. The catheter, with the guide wire 80 inserted through the bore of the catheter to stiffen the catheter tube can then be inserted into the cannula. The configuration of the cavity 32 and in particular the configuration of the distal end 34 of the cavity assists in guiding the catheter tube through the sheath of the cannula unit and reduces the amount of taxing hand to eve coordination necessary for introducing the catheter into a vein. When the catheter is fully inserted into the vein the ellipsoid portion 58 snap fits into the cavity 32 and maintains the catheter unit firmly attached to the cannula unit.

The fact that the docking device 58 securely fits into the cavity enables the cannula and the catheter to be taped together to a patients skin using the wings 31A and 31B of the cannula, as single unit. This eliminates the possibility of shearing of the catheter unit relative to the cannula unit which could occur if the cannula and catheter were separately taped to the skin.

Also, when correctly inserted into a vein, no portion of the fine bore silicone tube is exposed. This eliminates the possibility of the tube kinking.

Once the catheter is properly inserted and fixed to a patient's skin the guide wire is removed and the luer lock 51 can be connected to a suitable intravenous feeding mechanism.

FIGS. 5 to 16 show perspective and other views of a second embodiment of the present invention which operates on the same principle as the embodiment described in relation to FIGS. 1 to 4, although the design of the components is different.

Figure 5:
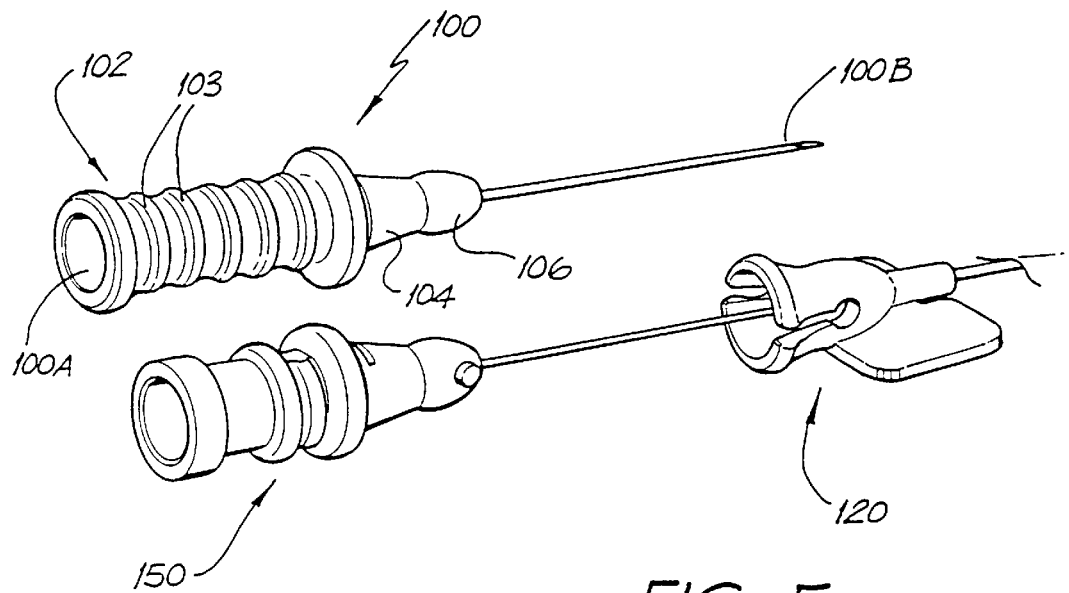
FIG. 5 is a perspective drawing of an introducer needle unit, a cannula, and catheter partially inserted into that cannula.
Figure 6:
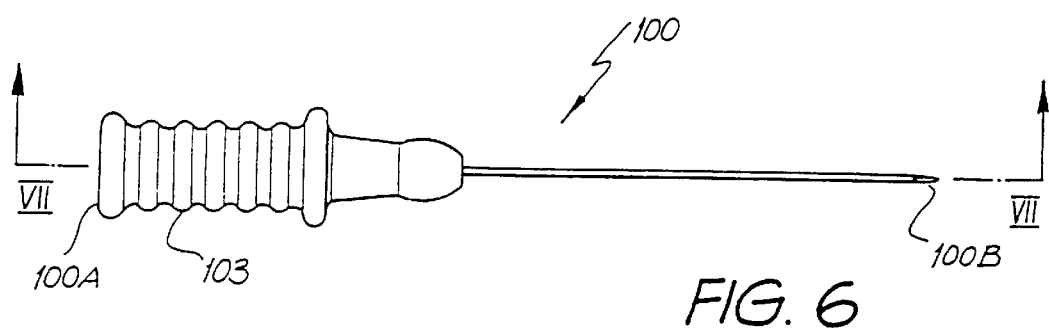
FIG. 6 is a plan view of the needle unit shown in FIG. 5.
Figure 7:
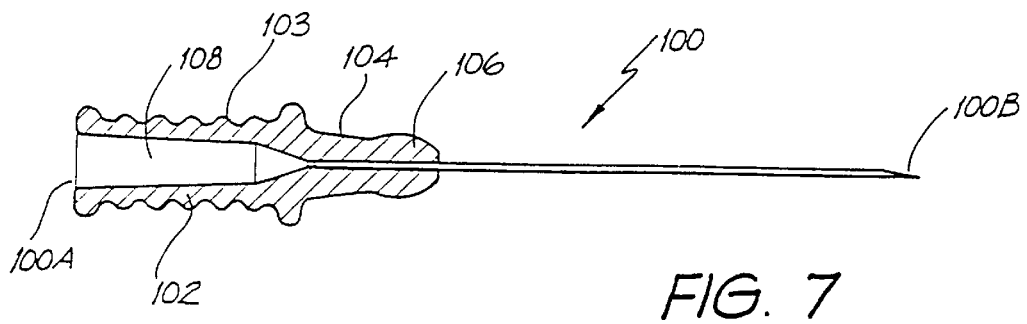
FIG. 7 is a sectional view on line VII of FIG. 6.
Figure 8:
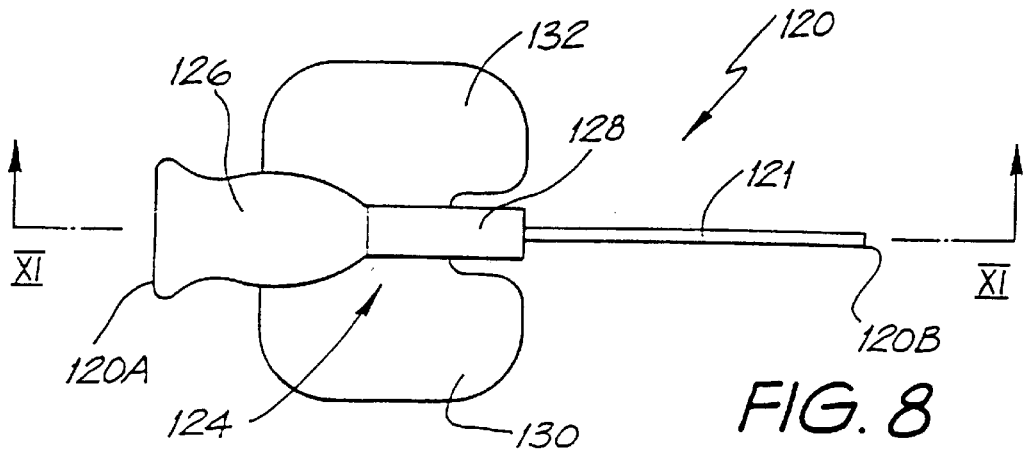
FIG. 8 is a plan view of the cannula shown in FIG. 5.
Figure 9:
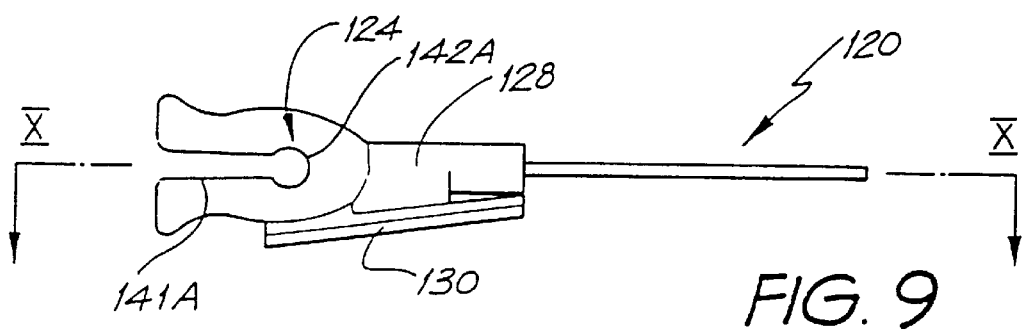
FIG. 9 is a side elevation of the cannula shown in FIGS. 5 and 8.

FIGS. 5 to 7 show a second embodiment of an introducing needle unit 100. The needle unit has a proximal end 100A and a distal end 100B. From the proximal end 100A of the needle unit the hub defines a main body portion 102 which is generally cylindrical but which is contoured with a series of circumferentially extending ribs 103, a conical portion 104 and an enlarged bulbous portion 106 which is generally ellipsoid. The proximal end of the cylindrical body portion defines a central bore 108 which is a standard luer taper. The bore can accept a breathing filter or stopper. As can be seen from FIG. 6 the needle extends from the distal end of the needle unit into the body of the hub as far as the junction between the conical portion and the cylindrical portion.

The needle is approximately 51 mm long and is made of surgical stainless steel. The hub of the needle unit is made from polycarbonate and is formed around the needle in a mould to manufacture the introducing needle unit 100.

Figure 10:
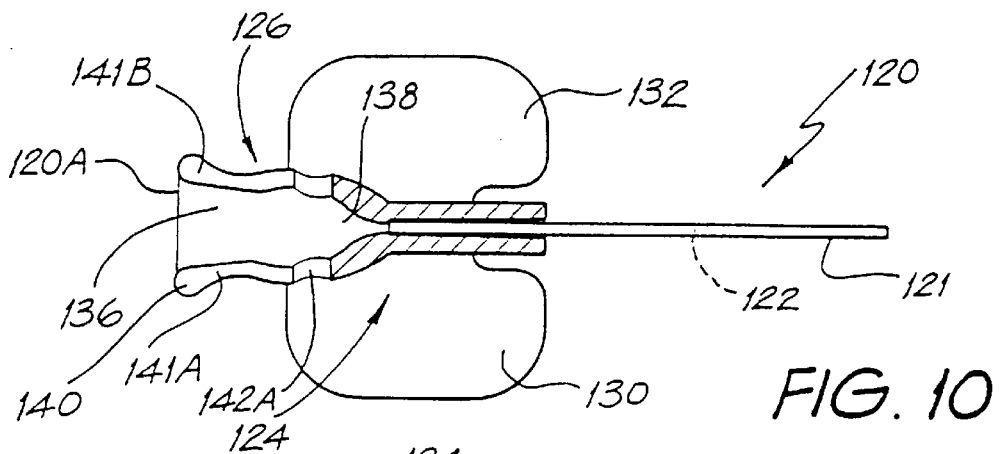
FIG. 10 is a sectional view on line X—X shown in FIG. 9.
Figure 11:
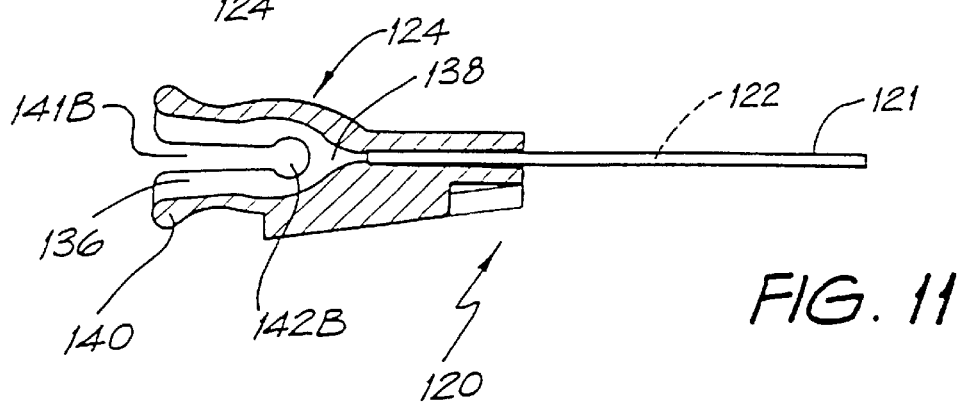
FIG. 11 is a sectional view on line XI—XI shown in FIG. 8.

FIGS. 9 to 12 show introducing a cannula unit 120 in more detail. The cannula has a proximal end 120A and a distal end 120B. It comprises a elongate sheath or tube 121 defining a cylindrical bore 122, and a hub portion generally indicated at 124. From the proximal end 120A the hub defines a generally bell shaped portion 126 followed by a generally cylindrical portion 128 from which extend two flat wing portions 130 and 132. As can be seen in FIGS. 10 and 11, the bell shaped portion 126 defines a generally bell shaped internal cavity 136 having an end portion 138 adjacent the tube 122 and a depending skirt portion 140. As can best be seen in FIG. 11 two slots 141A. 141B extend from the proximal end 120A of the hub of the cannula unit through the skirt portion 140. The slots are diametrically opposed on either side of the central axis of the cannula as defined by the bore 122 of the tube 121. The distal end of each slot terminates in an enlarged generally circular opening 142A, 142B, respectively.

The body of the cannula is made from moulded flexible nylon and the sheath of the cannula is made from polyamide tubing which is ultrasonically welded to the body of the cannula.

FIGS. 12 to 16 show the catheter unit 150 in more detail. The catheter unit has a proximal end 150A and a distal end 150B. Starting at the proximal end 150A of the catheter the body portion of the catheter defines a luer lock 152, a cylindrical portion 154, an annular rib 156, a generally cylindrical portion 158 but which includes opposed contoured surfaces 159A, 159B for grip, a second annular rib 160 of a slightly large diameter than the first annular rib, and a conical portion 162 which tapers towards a generally ellipsoid shaped protrusion or plug 164. As best seen in FIGS. 12 and 15 at the end of the catheter body portion remote from the proximal end of the catheter 150A, two diametrically opposed cylindrical stubs 166A, 166B protrude from the catheter.

The body of the catheter is polycarbonate. The catheter tube is glued to the catheter body by clear RV2 medical grade adhesive which is inserted into slot 170 shown in FIGS. 12 and 13.

The procedure for use of this second embodiment of the present invention is the same as that for the catheter shown in FIGS. 1 to 4. The introducing needle unit 120 is inserted in the introducing cannula unit 150 and the cannula unit and needle unit inserted into a vein. The needle is then removed from the cannula unit and the catheter fed into the cannula with the internal shape of the bell shaped cavity in the cannula unit acting as a guide means for assisting in guiding the silicone catheter tube 151 into the bore of the cannula. A guide wire 80 is used to stiffen the catheter tube. The stubs 166a, 166B on either side of the catheter hub pass along the slots 126A, 126B in the cannula enlarging the slots by pushing the two portions of the bell shaped portion apart and snap fit into the circular holes 142A, 142B. This prevents both rotation of the catheter hub in the cannula and longitudinal movement of the catheter relative to the cannula, in addition to the locking provided by the engagement of the ellipsoid portion 164 of the catheter in the correspondingly configured cavity 136 in the cannula. The catheter is thus locked to the cannula and the cannula can be taped to the skin of a patient.

The present invention provides a cannula unit which is specially shaped to guide a fine bore catheter into a vein without the need for taxing hand to eve coordination which is normally required when inserting fine bore catheters into veins.

The locking of the catheter and the cannula unit together, prevents the catheter from moving relative to the cannula and thus prevents shearing.

The catheter bore is of a constant diameter from the luer lock to the distal end of the catheter and this reduces the risk of blood products clotting the catheter bore.

The locking device on the catheter not only allows rapid attachment of the catheter to the cannula to produce a firmly locked device that can be fixed to the skin of the limb or truck of a person with tape but also provides protection from kinking or shearing of the catheter tube, since, inter ilia, none of the catheter tubing is exposed.

The following table shows exemplary dimensions for parts of the system shown in FIGS. 5 to 16.

| Introducing Needle | | Catheter Tube | | Cannula Sheath | |
| --- | --- | --- | --- | --- | --- |
| Outside Diameter | Internal Bore | Outside Diameter | Internal Bore Diameter | Internal Diameter | Outside Diameter |
| 0.600 mm | 0.400 mm | French Gauge 2 0.64 mm | 0.350 mm | 0.700 mm | 0.850 mm |
| 0.800 mm | 0.600 mm | French Gauge 3 0.90 mm | 0.600 mm | 1.000 mm | 1.150 mm |
| 1.00 mm | 0.800 mm | French Gauge 4 1.19 mm | 0.900 mm | 1.300 mm | 1.450 mm |

All the components of the system described above should be resistant to gamma sterilisation.

Although the above embodiments are described in terms of a fine bore catheter, it will be appreciated that although the invention is particularly suited to use with fine bore catheters the invention is also applicable to catheters having larger bores and diameters than fine bore catheters.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. Apparatus for introducing a fine bore catheter into a vein including a cannula unit comprising an elongate tubular sheath, the sheath defining a distal end and a proximal end, the cannula unit further comprising a hub enclosing the proximal end of the sheath, the cannula unit being adapted to receive an introducing needle for introducing the distal end of the sheath of the cannula into a vein; and a catheter unit, the catheter unit having a distal end and a proximal end, a body portion located at the proximal end of the catheter unit, and a catheter tube extending from the body portion to the distal end of the catheter unit characterised in that the catheter tube is a fine bore catheter tube having an outside bore less than 2.0 mm, in that the hub of the cannula unit defines guide means adapted to receive and guide the distal end of the catheter tube into the proximal end of the cannula sheath so that the catheter tube can be guided into and then fed along the sheath, and in that the hub of the cannula is adapted to receive and enclose at least a portion of the body of the catheter in a locking arrangement which substantially prevents the catheter body moving relative to the hub of the cannula unit.

2. Apparatus as claimed in claim 1 characterised in that the hub of the cannula defines a generally ellipsoid cavity or socket and the portion of the body of the catheter unit which is closest to the distal end of the catheter unit defines a generally ellipsoid protrusion or plug which is adapted to snap fit into the ellipsoid cavity to secure the catheter to the cannula.

3. Apparatus as claimed in claim 1 characterised in that the system includes an introducing needle unit adapted to locate inside the cannula sheath for use in inserting the cannula into a vein.

4. Apparatus as claimed in claim 2 characterised in that the hub of the cannula is generally bell shaped and defines a skirt portion and in that at least one slot extends through the skirt portion from the proximal end of the hub towards the distal end of the cannula parallel to the longitudinal axis of the hub and in that a stub extends from the ellipsoid portion of the catheter body which is adapted to locate in the slot the portion of the main body of the catheter which is inserted into the hub thereby assisting in guiding the main body of the catheter into the hub of the cannula and preventing rotation of the catheter body relative to the cannula hub.

5. Apparatus as claimed in claim 4 characterised in that a pair of diametrically opposed slots are provided in the skirt of the cannula and a pair of corresponding stubs extend from the catheter and in that the width of the stubs is greater than the width of the slot body so that the slots are enlarged as the stubs pass along the slots and in that the distal end of each slot is enlarged so that each stub snap fits into the enlarged distal ends of each respective slot.

6. Apparatus as claimed in claim 1 characterised in that the diameter of the bore of the catheter unit is substantially constant from the distal end of the catheter to a luer lock at the proximal end of the main body of the catheter.

7. Apparatus as claimed in claim 1 characterised in that the catheter tube is silicone and has an outside diameter of between 0.6 mm and 1.2 mm and an internal bore diameter of 0.3 mm to 0.8 mm.

8. Apparatus as claimed in claim 1 characterised in that the body of the catheter defines a slot which receives adhesive to secure the catheter tube to the body of the catheter.

9. A catheter unit, having a distal end and a proximal end, including a body portion located at the proximal end of the catheter unit, and a catheter tube extending from the body portion to the distal end of the catheter unit characterised in that the catheter tube is a fine bore catheter tube having an outside diameter of less than 2.0 mm and in that at least a portion of the body of the catheter is adapted to be received and enclosed in the hub of a cannula in a locking arrangement which substantially prevents the catheter body moving relative to the hub of the cannula unit.

10. A cannula unit for use in conjunction with the catheter of claim 9 comprising an elongate tubular sheath, the sheath defining a distal end and a proximal end, the cannula unit further comprising a hub enclosing the proximal end of the sheath, the cannula unit being adapted to receive an introducing needle for introducing the distal end of the sheath of the cannula into a vein; and characterised in that the hub of the cannula unit defines guide means adapted to receive and guide the distal end of a catheter tube into the proximal end of the cannula sheath so that the catheter tube can be guided into and then fed along the sheath, and in that the hub of the cannula is adapted to receive and enclose at least a portion of a body portion of the catheter in a locking arrangement which substantially prevents the catheter body moving relative to the hub of the cannula unit.

11. Apparatus for introducing a catheter into a vein including:

a cannula unit comprising an elongate tubular sheath, the sheath defining a distal end and a proximal end, the cannula unit further comprising a hub enclosing the proximal end of the sheath, the cannula unit being adapted to receive an introducing needle for introducing the distal end of the sheath of the cannula into a vein; and a catheter unit, the catheter unit having a distal end and a proximal end, a body portion located at the proximal end of the catheter unit, and a catheter tube extending from the body portion to the distal end of the catheter unit characterised in that the hub of the cannula unit defines guide means adapted to receive and guide the distal end of the catheter tube into the proximal end of the cannula sheath so that the catheter tube can be guided into and then fed along the sheath, and in that the hub of the cannula is adapted to receive and enclose at least a portion of the body of the catheter in a locking arrangement which substantially prevents the catheter body moving relative to the hub of the cannula unit.

12. Apparatus as claimed in claim 11 characterised in that the hub of the cannula defines a generally ellipsoid cavity or socket and the portion of the body of the catheter unit which is closest to the distal end of the catheter unit defines a generally ellipsoid protrusion or plug which is adapted to snap fit into the ellipsoid cavity to secure the catheter to the cannula.

13. Apparatus as claimed in claim 12 characterised in that the system includes an introducing needle unit adapted to locate inside the cannula sheath for use in inserting the cannula into a vein.

14. Apparatus as claimed in claim 13 characterised in that the hub of the cannula is generally bell shaped and defines a skirt portion and in that at least one slot extends through the skirt portion from the proximal end of the hub towards the distal end of the cannula parallel to the longitudinal axis of the hub and in that a stub extends from the ellipsoid portion of the catheter body which is adapted to locate in the slot the portion of the main body of the catheter which is inserted into the hub thereby assisting in guiding the main body of the catheter into the hub of the cannula and preventing rotation of the catheter body relative to the cannula hub.

15. Apparatus as claimed in claim 14 characterised in that a pair of diametrically opposed slots are provided in the skirt of the cannula and a pair of corresponding stubs extend from the catheter and in that the width of the stubs is greater than the width of the slot body so that the slots are enlarged as the stubs pass along the slots and in that the distal end of each slot is enlarged so that each stub snap fits into the enlarged distal ends of each respective slot.

16. Apparatus as claimed in claim 15 characterised in that the diameter of the bore of the catheter unit is substantially constant from the distal end of the catheter to a luer lock at the proximal end of the main body of the catheter.

17. Apparatus as claimed in claim 16 characterised in that the catheter tube is silicone and has an outside diameter of between 0.6 mm and 1.2 mm and an internal bore diameter of 0.3 mm to 0.8 mm.

18. Apparatus as claimed in claim 17 characterised in that the body of the catheter defines a slot which receives adhesive to secure the catheter tube to the body of the catheter.

* * * * *